(12) United States Patent
Jaggy et al.

(10) Patent No.: US 6,471,662 B1
(45) Date of Patent: Oct. 29, 2002

(54) ACOUSTIC THERAPY APPARATUS

(75) Inventors: Peter Jaggy, Oetisheim; Werner Krauss, Knittlingen; Edgar Bauer, Kraichtal, all of (DE)

(73) Assignee: Richard Wolf GmbH, Knittlingen (DE)

( * ) Notice: Subject to any disclaimer, the term of this patent is extended or adjusted under 35 U.S.C. 154(b) by 11 days.

(21) Appl. No.: 09/689,579

(22) Filed: Oct. 12, 2000

(30) Foreign Application Priority Data

Oct. 13, 1999 (DE) .......................... 199 49 426

(51) Int. Cl.[7] .............................. A61H 1/00; A61H 1/02; A61H 5/00
(52) U.S. Cl. ...................... 601/2; 601/6; 601/7; 604/22
(58) Field of Search ................................. 310/322, 323, 310/334; 601/12, 6, 7, 46, 48; 604/22

(56) References Cited

U.S. PATENT DOCUMENTS

| | | | | |
|---|---|---|---|---|
| 5,409,446 A | * | 4/1995 | Rattner | 600/459 |
| 5,545,124 A | * | 8/1996 | Krause et al. | 601/2 |
| 5,792,078 A | * | 8/1998 | Rattner | 600/427 |
| 5,941,838 A | * | 8/1999 | Eizenhofer | 367/175 |
| 6,325,769 B1 | * | 12/2001 | Klopotek | 601/2 |

* cited by examiner

*Primary Examiner*—Marvin M. Lateef
*Assistant Examiner*—Jeoyuh Lin
(74) *Attorney, Agent, or Firm*—Cohen, Pontani, Lieberman & Pavane

(57) ABSTRACT

An acoustic therapy device is provided including a housing, an electro-acoustic transducer, a coupling element and coupling cushions. The electro-acoustic transducer is arranged in the housing which includes a shell. The coupling element has a coupling surface flush with edges of the shell. Another coupling surface of the coupling element is on the sound irradiation surface of the transducer and sound waves from the sound irradiation surface are directly coupled into the coupling element. An elastic coupling cushion is connected to a surface of the coupling element. One coupling surface of the coupling element and an exterior coupling surface of the coupling cushion define a sound advance path the length of which may, along with a penetration depth of the sound waves, be varied.

7 Claims, 4 Drawing Sheets

ACOUSTIC THERAPY APPARATUS

BACKGROUND OF THE INVENTION

1. Field of the Invention

The invention relates an acoustic therapy apparatus with an electro-acoustic transducer for producing focused sound waves to be transmitted onto the body of a patient via coupling media. The coupling media and the transducer, where appropriate, in combination with parts of a transducer housing, form a shell and comprise a carrier equipped with transducer elements. Sound waves exiting the sound irradiation surface are directly coupled into a coupling element which bears on this irradiation surface, is fixedly allocated to the transducer and forms a first sound advance path. After running through the coupling element the sound waves are further coupled into an elastic coupling cushion which is to be applied on to the patient body, is releasably connected to the coupling element and forms a second acoustic sound advance path. The length of the respective external sound advance path and thus the penetration depth of the sound waves into the patient body is variable by using one of several available coupling cushions of various thicknesses:

2. Description of the Related Art

Most of the apparatus described above are equipped with self-focused transducers where it is particularly important to bring the transducer focus coincident with the treatment location in the patient body. In an apparatus with a stationary transducer focus, this may be problematic since the objects to be irradiated with sound.

For this reason the apparatus is modified so that the sound advance path i.e., the path between the sound irradiation surface of the transducer and the surface at which the sound is coupled into the body of the patient is variable. For this purpose the apparatus are provided with at least one coupling element having an end surface on the transducer irradiation surface and an other end surface forming a coupling surface to be applied onto the patient body.

The length of the advance path is determined by the respective distance between the two mentioned end surfaces, by which means the distance between the coupling surface of the coupling element and the transducer focus, as well as the respective penetration depth or position of the sound wave focus in the patient body, is predetermined. The mentioned distances and the sound penetration depth may be changed by variation of the length of the sound advance path.

German reference DE 195 09 004 C1 discloses exchangeable coupling elements having different thicknesses and that form sound advance paths that vary in length. In each case, one shape stable and elastic coupling element selected with respect to a suitable advance path is incorporated into the transducer shell in an axially aligned manner such that its end surface as a or interior surface comes to bear against the sound irradiation surface of the transducer whilst the oppositely lying end surface located outside the transducer shell or transducer housing serves as a sound coupling surface via which the sound is irradiated and coupled into the patient body in a focused manner.

With this known therapy apparatus a transition free of air bubbles between the sound irradiation surface and the coupling element even with the additional application of a coupling gel may be difficult to achieve. Furthermore the large-volumed coupling elements consisting of a hydro-gel have quite a large weight which is why they are difficult to manipulate during assembly and disassembly.

German reference DE 33 12 014 A1 discloses a therapy apparatus. with which a relatively large volumed coupling element is permanently and rigidly allocated to the transducer and further light coupling cushions of various thicknesses in the form of elastic disks may be exchangeably connected to the coupling element. In this case the effective length of the sound advance path is determined by the sum of the thicknesses of the coupling element and of the coupling cushion and is variable by using coupling cushions of differing thicknesses.

Air bubbles in the region of the sound transition from the sound irradiation surface of the transducer to the coupling element are also expected after incorporation of the coupling element into the transducer shell. These air bubbles, which disturb sound propagation may not be alleviated when the elastic coupling element is rigidly pressed against the sound irradiation surface. Furthermore, germs can get into the region between the transducer or transducer housing and the coupling element so that it becomes necessary to periodically remove and disassemble the coupling element to clean and sterilize it.

German reference DE 33 19 87 102 discloses a therapy apparatus including an advance path of soft plastic and a coupling cushion filled with water for coupling the sound waves into the body of the patient. For the purpose of varying the penetration depth of the therapy waves, the water volume in the coupling cushion must be varied via a compensation vessel. It is particularly difficult to fill the spherical calotte and transducer shell with the plastic since the plastic filling projects relatively far beyond the transducer shell to the outside in the sound direction. On the side facing the coupling cushion, the coupling element must be formed convexly or conically in a projecting manner in order to let air bubbles in the coupling cushion or coupling pillow wander laterally out of the sound field. As with all therapy apparatus functioning with water as a coupling medium, one must also deal with the possibility of contaminated water.

BRIEF SUMMARY OF THE INVENTION

The object of the present invention is to overcome the disadvantages of the prior art.

Another object of the present invention is to provide a therapy apparatus that is easy to manipulate and does not have air bubbles.

A further object of the present invention is to provide a therapy apparatus whereby cleaning and sterilization of the coupling element can be performed while the coupling element remains in the transducer shell.

These objects are achieved in the present invention whereby the transducer shell, with the material of the coupling element, is permanently cast flush with the edge and filled out. The casting of the transducer shell is performed under a vacuum so that the material of the coupling element gets into contact with the transducer shell surface without air bubbles and assumes a permanent adhesive connection to it.

If the coupling element fills out the transducer shell flush with the edge a planar or when required a slightly curved coupling surface of the coupling element, results that is easy to clean and, where required, is easy to sterilize.

The transducer shell may simply be completely filled out with the material of the coupling element, and subsequent to this the transducer shell and the surface is removed of its filling in a planar manner with a spatula so that there arises a surface which occludes flush with the edge of the transducer shell. It is also ensured that the filling mass remains shape stable in the transducer shell. If the coupling element incorporated in this manner into the transducer shell becomes damaged material may simply be in the region of such damage and brushed smooth so that repairs are possible in a simple and inexpensive manner.

As has already been mentioned the coupling surface of the coupling element located in the transducer shell may also be curved slightly in a convex or concave manner. However, a planar coupling surface is preferred since it offers the smallest possible surface and thus the danger that air bubbles remain between the coupling element and the coupling cushion to be laid onto this is reduced to is minimized.

Hydro-gels and the like are a suitable material for the coupling element and the coupling cushion. A polyacrylamide agar gel is preferred. Furthermore, technical silicon gel materials, synthetic rubber materials and polyurethane materials are particularly suited to this use as they set well and possess the necessary elasticity. In any case, the coupling element may be formed of a hard elastic and the coupling element may be formed of a soft elastic. It is sufficient to determine the position of the therapy zone with a standard ultrasound locating apparatus and to mark this on the patient body using target marking and then to apply the suitable coupling cushion.

The releasable connection of the coupling cushion to the coupling element is then created such that the coupling surface of the coupling element and the interior coupling surface of the coupling cushion, are connectable by an adhesive effect produced by a vacuum between these two surfaces. This may be effected via a suction pad effect if, for example, the coupling surface of the coupling element is planar and the coupling-in surface of the coupling cushion is concave or, conversely if the coupling surface of the coupling element is concave and the coupling surface of the coupling cushion is planar, in which case the two surfaces by way of pressure on the coupling cushion are brought into mutual bearing on one another in a close and bubble-free manner and are held together by the suction effect.

In the coupling element there may also be formed suction channels which end in the coupling surface of the coupling element and may be connected via a valve to a suction pump, through which either air or water as a coupling medium is suctioned from between the coupling cushion and the coupling element. A vacuum between the coupling cushion and the coupling element which is required for the adhesive connection is thus maintained.

Furthermore, the transducer housing accommodating the carrier with the transducer elements should laterally encase the coupling element so that in this case the transducer shell below is limited by the sound irradiation surface and laterally by the transducer housing.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further noted that the drawings are merely intended to conceptually illustrate the structures and procedures described herein.

BRIEF DESCRIPTION OF THE DRAWINGS

The present invention will be described in greater detail below, with reference to the drawings in schematic form, wherein like numerals represent like elements.

DETAILED DESCRIPTION OF THE PRESENTLY PREFERRED EMBODIMENTS

Figure 1:
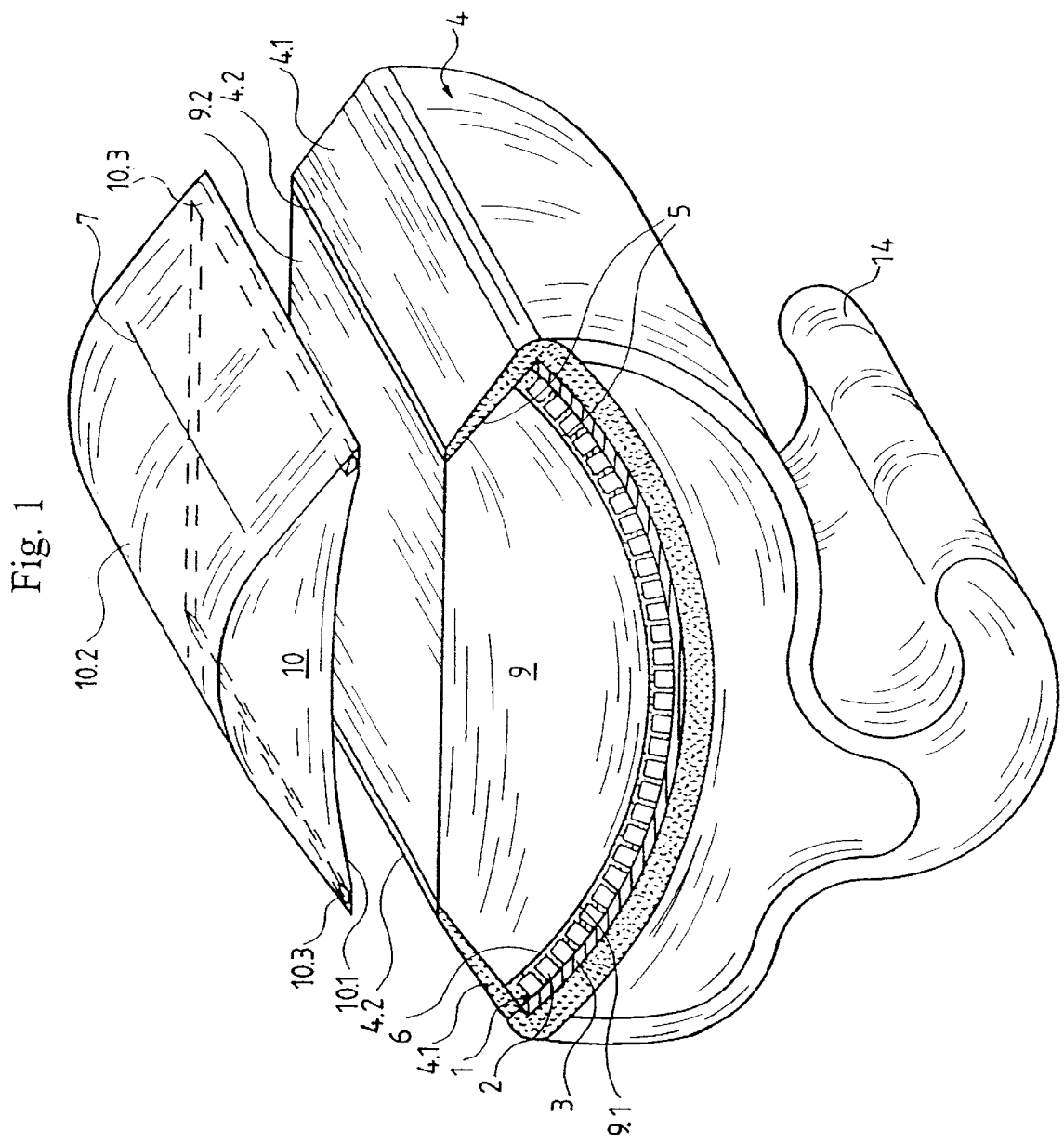
FIG. 1 is an embodiment of a therapy apparatus according to the present invention having sound focused on a line.

The shown therapy apparatus are equipped with self-focusing electro-acoustic transducers 1 which consist in the known manner essentially of a concavely curved metal carrier 3 equipped with piezo-electric transducer elements 2 and in combination with edge regions 4.1 of a transducer housing 4 form a shell 5. According to FIGS. 1 to 3, these are in the shape of an elongate trough with the apparatus according to FIG. 4 being in the shape of a spherical calotte.

The trough shape results when the sound irradiation surface 6 has the shape of a part surface area of a regular cylinder, the sound irradiation surface 6 thus only has a single plane of symmetry and the sound is focused onto a line 7. It is clear that the thus shaped irradiation surface results automatically when the carrier 3 as such is formed as a part regular cylinder. The therapy apparatus according to FIG. 4 has a spherical calotte shaped carrier so that the irradiation surface 6 is necessarily a spherical calotte surface. In this case the sound runs in the direction of the focus point 8.

In all of the therapy apparatus, a coupling element 9 is fixedly integrated in the transducer shell 5. The coupling element 9 is made by casting the transducer shell with the coupling element to contact a coupling surface 9.1 against the irradiation surface 6 of the transducer and an inner surface of the edge regions 4.1 of the transducer housing 4. The coupling element 9 fills out the transducer shell up to its edge 4.2 (FIGS. 1 to 3) in a flush manner so that a planar or slightly concavely curved coupling surface 9.2 arises for a coupling cushion 10.

The coupling cushion 10 has an interior coupling surface 10.1 with which it may be fastened on the coupling surface 9.2 of the coupling element. Furthermore the coupling cushion has an exterior surface 10.2 which is applied onto the body of the patient and via which the sound waves, for example shock or pressure waves, are coupled into the patient body. Since the coupling cushion 10 consists of soft elastic material, it may be useful to provide it with stiffening elements 10.3.

The sound advance path is determined by the predetermined set thickness of the coupling element 9 and the thickness of the coupling cushion 10. As has already been mentioned previously several coupling cushions of varying thicknesses are held available in order to be able to vary and determine the length of the advance path with regard to how deep the focus line 7 or the focus point 8 should lie in the patient body.

With the therapy apparatus shown in FIG. 1 the coupling surface 9.2 of the coupling element is planar whilst the interior surface 10.1 of the coupling cushion 10 is concavely curved so that the coupling cushion in the manner of a suction pad may be pressed onto the coupling element 9 and by way of a suction effect be connected to it.

Figure 2:
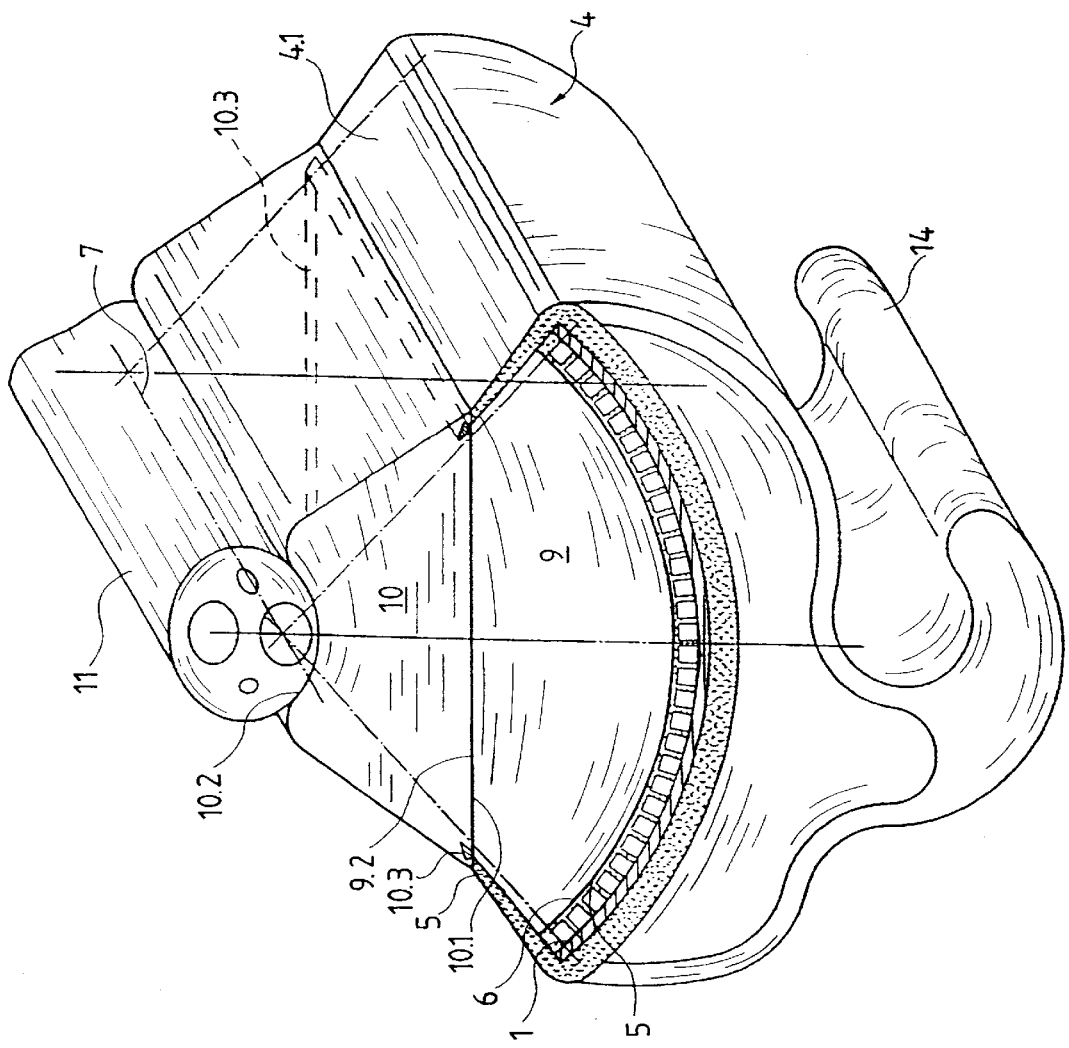
FIG. 2 is a further embodiment of a therapy apparatus according to the present invention having sound focused on a line.

As is deduced from FIG. 2 the coupling surface of the coupling cushion may be adapted to the anatomical particularities of an extremity or a body member 11 of the patient in that roughly according to the representation the coupling element is formed as an elongate trough into which the body part to be irradiated is applied.

Figure 3:
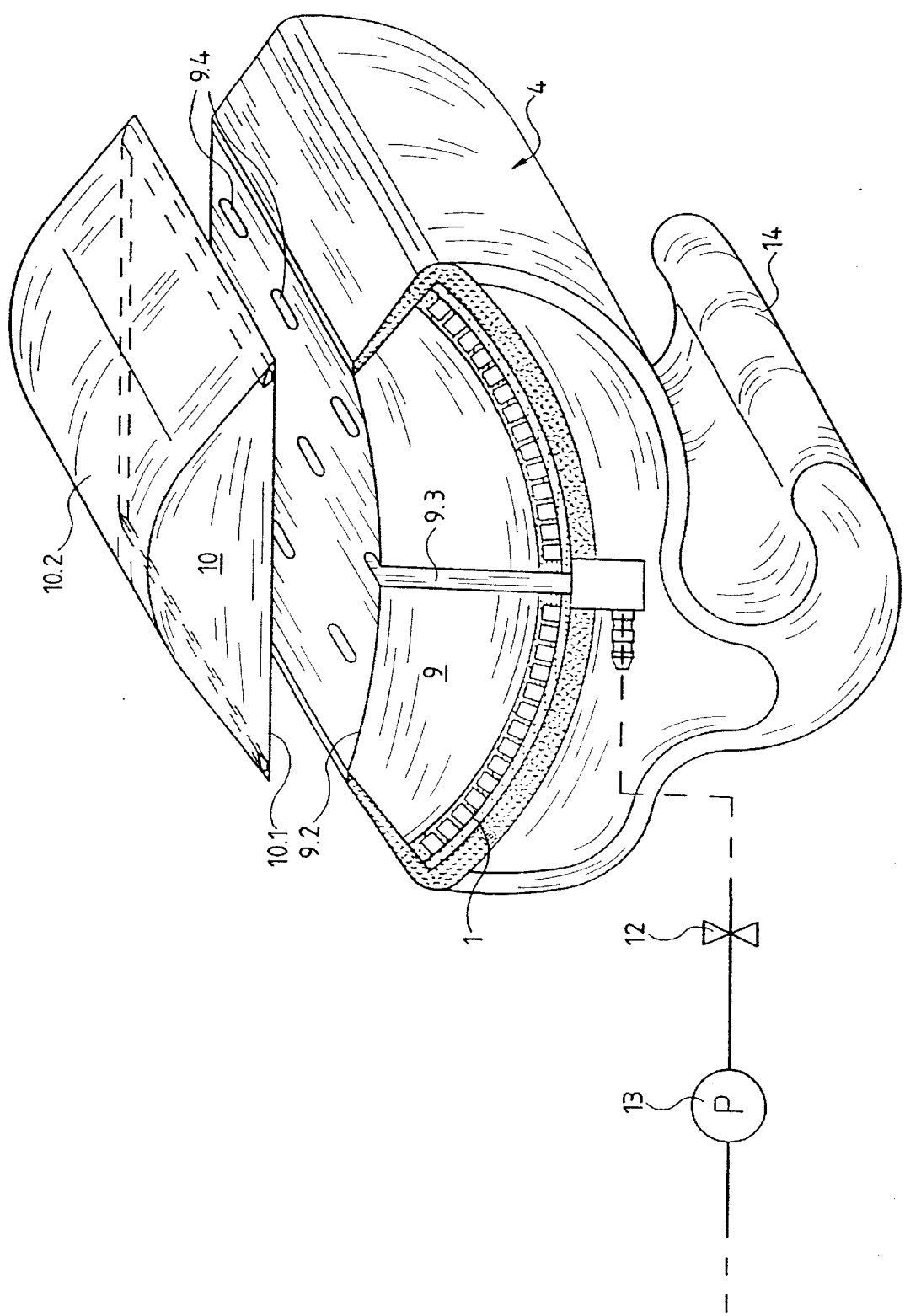
FIG. 3 is a further embodiment of a therapy apparatus according to the present invention having sound focused on a line.
Figure 4:
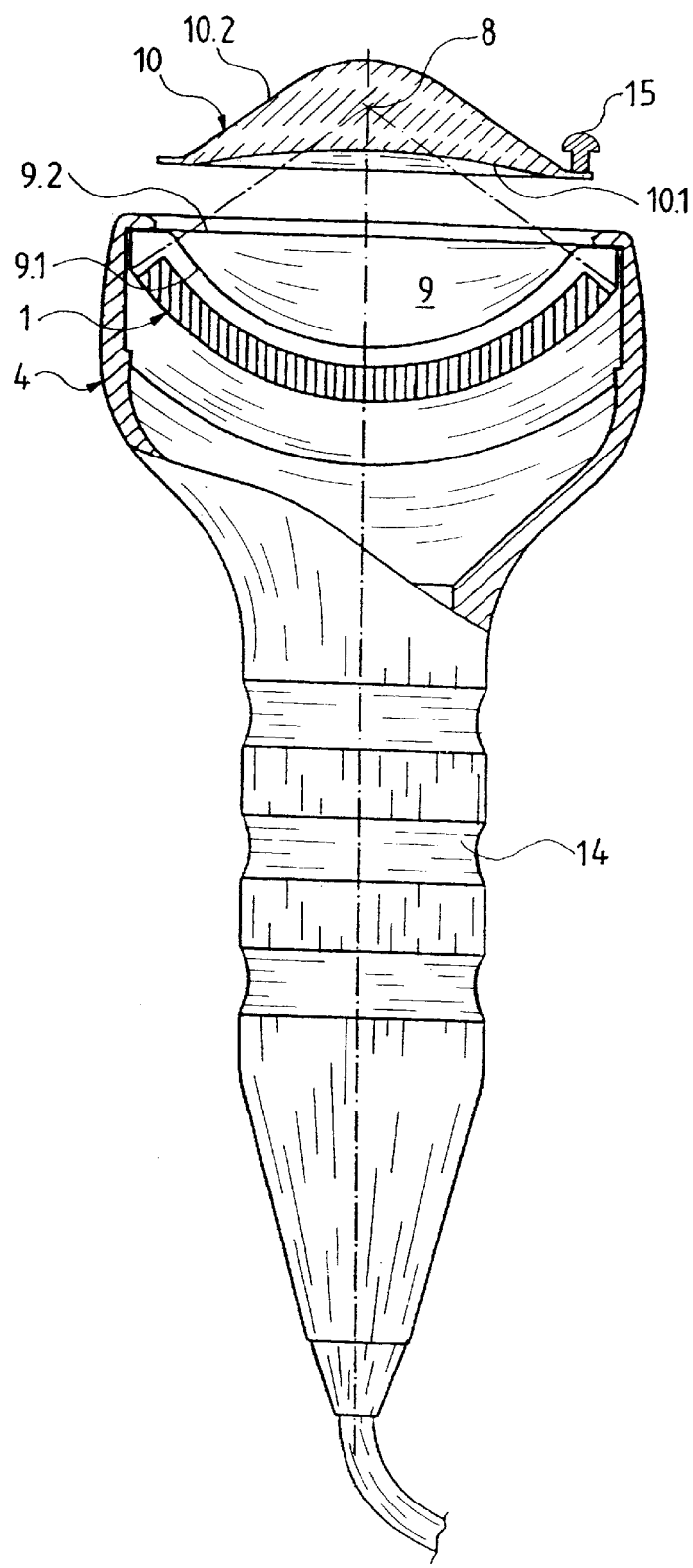
FIG. 4 is a further embodiment of a therapy apparatus according to the present invention having sound focused on a point.

Turning now to FIG. 3, an embodiment having suction channels 9.3 in the coupling element 9 is shown. Suction channels 9.3 contact the coupling surface 9.2 via openings 9.4 and are connected to a suction pump 13 at the other end via a valve 12.

With a coupling cushion 10 applied onto the coupling element 9 via the openings 9.3 coupling fluid for improving the adhesive effect is located between the coupling cushion and the coupling element. This fluid may be suctioned away so that the coupling cushion may be suctioned free of air against the coupling surface 9.2 and specifically with the valve 12 opened and with a running pump 13. This suctioning is terminated by closing the valve 12, whilst after the treatment procedure the valve 12 is again opened and the vacuum causing the adhesive effect is lifted and the coupling cushion 10 may be easily lifted from the coupling element 9. Usefully the suction channels at least during the treatment procedure remain filled with the coupling fluid so that in the coupling element 9 there no air-filled spaces which would prevent and unfavorably influence sound propagation.

If the therapy apparatus is designed as a small hand-operated apparatus it is useful to provide it with a handle or grip part 14. Furthermore, the coupling cushion 10 on the edge region according to FIG. 4 may be provided with a handle 15 which simplifies the lifting and pulling away of the coupling cushion from the coupling element by hand.

Thus, while there has been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An acoustic therapy apparatus, comprising:

a housing;

an electro-acoustic transducer having a sound irradiation surface and elements, the transducer being operatively arranged in a housing, whereby the housing forms a shell having edge regions and has a carrier for the transducer elements;

at least one coupling element having a first coupling surface and a second coupling surface, the coupling element being cast in the shell of the housing and filling the shell such that the second coupling surface is flush with the edge regions of the shell and the first coupling surface is fixedly arranged on the sound irradiation surface of the transducer, wherein sound waves from the sound irradiation surface are directly coupled into the coupling element; and an elastic coupling cushion having an interior coupling surface and an exterior coupling surface, the coupling cushion being releasably connected to the second coupling surface of the coupling element, the first and second coupling surfaces of the coupling element defining a first sound advance path therebetween, while the the interior and exterior coupling surfaces of the coupling cushion define a second sound advance path therebetween, whereby both a length of the second sound advance path and a penetration depth of the sound waves are variable in dependence upon the thickness of the coupling cushion.

2. The apparatus according to claim 1, wherein the coupling element comprises a hard elastic material and the coupling cushion comprises a soft elastic material.

3. The apparatus according to claim 1, wherein the second coupling surface of the coupling element is planar and the interior coupling surface of the coupling cushion is concave.

4. The apparatus according to claim 1, wherein the carrier and the housing laterally encase the coupling element.

5. An acoustic therapy apparatus, comprising:

a housing;

an electro-acoustic transducer having a sound irradiation surface and elements, the transducer being operatively arranged in a housing, whereby the housing forms a shell having edge regions and has a carrier for the transducer elements;

at least one coupling element having a first coupling surface and a second coupling surface, the coupling element being operatively arranged in the shell of the housing and the second coupling surface being flush with the edge regions of the shell, wherein the first coupling surface is fixedly arranged on the sound irradiation surface of the transducer so that sound waves from the sound irradiation surface are directly coupled into the coupling element; and an elastic coupling cushion having an interior coupling surface and an exterior coupling surface, the coupling cushion being releasably connected to the second surface of the coupling element, the first and second coupling surfaces of the coupling element defining a first sound advance path therebetween, while the interior and exterior coupling surfaces of the coupling cushion define a second sound advance path therebetween, whereby both a length of the second sound advance path and a penetration depth of the sound waves are variable in dependence upon the thickness of the coupling cushion, wherein the second coupling surface of the coupling element and the interior coupling surface of the coupling cushion are connectable by a vacuum produced between the surfaces.

6. The apparatus according to claim 5, wherein the second coupling surface of the coupling element is planar and the interior coupling surface of the coupling cushion is planar.

7. The apparatus according to claim 5, further comprising:

a suction pump; and a valve operatively attachable to the suction pump, wherein the coupling element further comprises a plurality of suction channels, a first end of the suction channels being open at the interior coupling surface of the coupling element and a second end of the suction channels being selectively connectable to the suction pump via the valve.

* * * * *